United States Patent [19]

Kunz

[11] 4,069,262

[45] Jan. 17, 1978

[54] PREPARATION OF 2-FLUORONITROBENZENE

[75] Inventor: Robert Allison Kunz, Media, Pa.

[73] Assignee: E. I. Du Pont de Nemours and Company, Wilmington, Del.

[21] Appl. No.: 775,038

[22] Filed: Mar. 7, 1977

[51] Int. Cl.$^2$ .............................. C07C 79/12
[52] U.S. Cl. ............................. 260/646
[58] Field of Search ........................ 260/646

Primary Examiner—Leland A. Sebastian

[57] ABSTRACT

An improved process for preparing 2-fluoronitrobenzene by reacting 2-chloronitrobenzene with ultra-fine particulate potassium fluoride in tetramethylene sulfone with a macrocyclic ether or a quaternary ammonium halide catalyst. 2-fluoronitrobenzene is an intermediate useful in the preparation of certain known herbicides.

13 Claims, No Drawings

PREPARATION OF 2-FLUORONITROBENZENE

BACKGROUND OF THE INVENTION 2-fluoronitrobenzene is useful as an intermediate in the preparation of certain known herbicides, such as the 2-substituted aryl-4,5,6,7-tetrahydro-2H-isoindole-1,3-diones disclosed in U.S. Pat. No. 4,001,272, granted on Jan. 4, 1977 to Steven J. Goddard.

2-fluoronitrobenzene has, heretofore, been prepared by three different basic synthetic methods. The first method involves the nitration of fluorobenzene using a mixture of sulfuric acid and nitric acid. However, the product obtained from this method is an isomeric mixture of 4-fluoronitrobenzene and 2-fluoronitrobenzene, typically in a 9:1 ratio.

The second method involves the diazotization of 2-nitroaniline and conversion to 2-nitrodiazonium fluoroborate. The thermal decomposition of the dry diazonium fluoroborate gives 2-fluoronitrobenzene in only 10-19% yield. The thermal decomposition of diazonium fluoroborates is dangerous and proceeds in low yield when there is a nitro group in the position ortho to the diazonium group.

The third method is based on the halogen exchange of 2-chloronitrobenzene with an alkali metal fluoride. The halogen exchange reaction can be conducted both with and without solvent. Previous methods, however, require long reaction times and high temperatures, give only moderate yields of 2-fluoronitrobenzene, and/or require the use of rare alkali metal fluorides such as cesium or rubidium fluoride.

U.S. Pat. No. 3,240,824 discloses a process for preparing 2-fluoronitrobenzene in 60.6% yield (based on 50.5% conversion) by heating under pressure, equimolar amounts of 2-chloronitrobenzene and potassium fluoride without solvent at 290° C for 24 hours.

Finger and Kruse [*J. Amer. Chem. Soc.*, 78 6034 (1956)] disclose a process for preparing 2-fluoronitrobenzene in dimethylformamide at 170° C for 163 hours in 40% yield, and in dimethylsulfoxide at 185° C for 4.5 hours in 38% yield.

Fukui et al. [*Nippon Kagaku Zasski,* 79, 889 (1958)];[Chemical Abstracts, 54, 4430 c (1958)] improves upon the yield reported above in a dimethylsulfoxide system. Fukui maintains the reaction temperature at 185° C for 10 hours and reports a 56% yield.

Fuller [German Offenlegungsschrift No. 2,527,944 (1975)] was the first to disclose the preparation of 2-fluoronitrobenzene by reaction of 2-chloronitrobenzene with potassium fluoride in a tetramethylene sulfone (sulfolane) solvent, although others had reported earlier the use of sulfolane as the solvent for fluorination (with potassium fluoride) of other materials. For example, Fuller [*J. Chem. Soc.*, 6264 (1965)] discloses fluorination of hexachlorobenzene and Matsui et al. [Japanese Kokai, 74/110,637] discloses fluorination of 4-chloronitrobenzene (with a catalytic amount of cesium fluoride) in sulfolane. Fuller's preparation of 2-fluoronitrobenzene is conducted at 240° C for 22 hours and results in a 60.5% yield.

All previous methods for preparing 2-fluoronitrobenzene by halogen exchange have one or more of the disadvantages mentioned above; that is, they require long reaction times and/or high temperatures, give only moderate yields of the desired product, and/or require the use of rare alkali metal fluorides such as cesium or rubidium fluoride.

SUMMARY OF THE INVENTION

The present invention concerns an improved process for the preparation of 2-fluoronitrobenzene by heating 2-chloronitrobenzene with ultra-fine particulate potassium fluoride in sulfolane, with a catalyst selected from the group consisting of macrocyclic ethers and quaternary ammonium halides, at a temperature of 240° to 250° C. The process of the present invention results in conversion of the 2-chloronitrobenzene to 2-fluoronitrobenzene with shorter reaction time and higher yield and uses less solvent than previously known processes, such as those discussed above.

DETAILED DESCRIPTION OF THE INVENTION

Preferably, the molar ratio of 2-chloronitrobenzene to sulfolane is 1 : 1–0.3, the reaction temperature is 240° to 250° C, and the molar ratio of 2-chloronitrobenzene to potassium fluoride is 1 : 1.1–1.5. A catalyst is chosen from the group consisting of macrocyclic ethers, such as 1,4,7,10,13,16-hexaoxacyclooctadecane, and quaternary ammonium halides, such as benzyltriethylammonium chloride. The reaction time is 2–8 hours.

The molar ratio of sulfolane to 2-chloronitrobenzene is particularly important. If the molar ratio of sulfolane to 2-chloronitrobenzene is less than 0.3 : 1, the rate of the reaction is significantly decreased; while a ratio greater than 1 : 1, significantly decreases the yield of 2-fluoronitrobenzene due to the formation of by-products. The preferred molar ratio of 2-chlorobenzene to sulfolane is 1 : 0.9–1.0.

The molar ratio of 2-chloronitrobenzene to potassium fluoride is not quite so important. Nevertheless, an excess of potassium fluoride beyond that specified above, for example 1 : 2, is not necessary and will not lead to a greater conversion of 2-chloronitrobenzene to 2-fluoronitrobenzene. However, the particle size of the potassium fluoride is quite important and should be 1–20 microns. Larger particle sizes give significantly decreased yields. The potassium fluoride should not be caked together as this will lower the yield of the reaction. It is desirable that the potassium fluoride contain less than 0.1% by weight water since this will minimize caking.

The reaction temperature and reaction time are also quite important, and when the reaction temperature is less than 240° C, the reaction will not give sufficient conversion. At temperatures above 250° C, the formation of by-products becomes significant and will lower the yield of 2-fluoronitrobenzene. When the reaction time is less than 2 hours, the reaction will not give sufficient conversion. With reaction times greater than 8 hours, the formation of by-products becomes significant and will lower the yield of 2-fluoronitrobenzene.

A macrocyclic ether, such as 1,4,7,10,13,16-hexaoxacyclooctadecane (18-crown-6 ether), may be used as the catalyst. Preferred conditions when such a catalyst is used are 2-chloronitrobenzene, potassium fluoride, macrocyclic ether, and sulfolane in a molar ratio of 1 : 1.1–1.5 : 0.001–0.01 : 0.3–1.0, heated at 240°–250° C for 2–8 hours. Most preferred conditions are 2-chloronitrobenzene potassium fluoride, 18-crown-6 gl ether, and sulfolane in a molar ratio of 1 : 1.1–1.5 : 0.002–0.004 : 1, heated in 240°–242° C for 4–6 hours.

Alternatively, a quaternary ammonium halide, such as tetrabutylammonium chloride, benzyltrimethylammonium chloride, benzyltrimethylammonium fluoride or benzyltriethylammonium chloride, may be used as the catalyst. Preferred conditions when such a catalyst is used are 2-chloronitrobenzene, potassium fluoride, quaternary ammonium halide, halide, and sulfolane in a molar ratio of 1 : 1.1–1.5 : 0.01–0.05 : 0.3–1.0, heated at 240°–250° C for 2–8 hours. Most preferred conditions are 2-chloronitrobenzene, potassium fluoride, benzyltriethylammonium chloride, and sulfolane in a molar ratio of 1 : 1.1–1.5 : 0.02–0.03 : 1.0, heated at 240°–242° C. for 4–8 hours.

2-fluoronitrobenzene and unreacted 2-chloronitrobenzene can be separated from the reaction mixture by either of two methods. In the first of these methods the reaction mixture is steam distilled to give 2-fluoronitrobenzene and unreacted 2-chloronitrobenzene in the distillate and inorganic salts, sulfolane, and tars in the residue. The steam distillate is then separated into layers, and the organic layer is distilled through a suitable fractionating column to separate the 2-fluoronitrobenzene from the unreacted 2-chloronitrobenzene.

An alternative method for obtaining 2-fluoronitrobenzene from the reaction mixture is fractional distillation, whereby the sulfolane is recovered for reuse. The reaction mixture is filtered to separate the inorganic salts and the filter cake is washed with a suitable solvent such as sulfolane or methylene chloride. The filtrate and washings are then fractionally distilled with a suitable fractionating column to separate the 2-fluoronitrobenzene, unreacted 2-chloronitrobenzene and sulfolane.

In the following illustrative examples, all parts and percentages are by weight, unless specified otherwise.

EXAMPLES 1

A mixture of 158 parts 2-chloronitrobenzene, 90 parts potassium fluoride, 0.5 parts 18-crown-6 ether, and 120 parts sulfolane were heated together at 240° C for 4 hours. Gas chromatography of the reaction mixture showed 78.6% 2-fluoronitrobenzene annd 21.3% 2-chloronitrobenzene.

EXAMPLE 2

A mixture of 158 parts 2-chloronitrobenzene, 90 parts potassium fluoride, 1 part 18-crown-6 ether, and 120 parts sulfolane were heated together at 240° C for 4 hours. Gas chromatography of the reaction mixture showed 87.2% 2-fluoronitrobenzene and 12.8% 2-chloronitrobenzene.

EXAMPLE 3

A mixture of 158 parts 2-chloronitrobenzene, 90 parts potassium fluoride, 7 parts benzyltriethylammonium chloride and 120 parts sulfolane were heated together at 240° C for 6 hours. Gas chromatography of the reaction mixture showed 67.6% 2-fluoronitrobenzene and 32.4% 2-chloronitribenzene.

I claim:

1. A process for preparing 2-fluoronitrobenzene which comprises heating a mixture of 2-chloronitrobenzene potassium fluoride of particle size 1–20 microns and a catalyst in sulfolane for 2–8 hours at 240°–250° C wherein the molar ratio of 2-chloronitrobenzene to potassium fluoride to sulfolane is 1 : 1.1–1.5 : 0.3–1.0.

2. The process of claim 1 wherein the reaction is carried out at 240°–242° C and the molar ratio of 2-chloronitrobenzene to potassium fluoride to sulfolane is 1: 1.1–1.5 : 0.9–1.0.

3. The process of claim 1 wherein the catalyst is selected from the group consisting of macrocyclic ethers and quaternary ammonium halides.

4. The process of claim 2 wherein the catalyst is selected from the group consisting of macrocyclic ethers and quaternary ammonium halides.

5. The process of claim 4 wherein the catalyst is 1,4,7,10,13,16-hexaoxacyclooctadecane and the molar ratio of 2-chloronitrobenzene to catalyst is 1 : 0.001–0.01.

6. The process of claim 5 wherein the reaction is carried out at 240°–242° C.

7. The process of claim 5 wherein the molar ratio of 2-chloronitrobenzene to catalyst is 1 : 0.002–0.004.

8. The process of claim 7 wherein the reaction is carried out at 240°–242° C.

9. The process of claim 4 wherein the catalyst is a quaternary ammonium halide and the molar ratio of 2-chloronitrobennzene to catalyst is 1 : 0.01–0.05.

10. The process of claim 9 wherein the catalyst is selected from the group consisting of tetrabutylammonium chloride, benzyltrimethylammonium fluoride, or benzyltriethylammonium chloride.

11. The process of claim 10 wherein the reaction is carried out at 240°–242° C.

12. The process of claim 10 wherein the molar ratio of 2-chloronitrobenzene to catalyst is 1 : 0.02–0.03.

13. The process of claim 12 wherein the reaction is carried out at 240°–242° C.

* * * * *